United States Patent [19]

Brown et al.

[11] 4,183,958
[45] Jan. 15, 1980

[54] FUNGICIDAL 1-(ALKOXYPHENYL)-5-(SUBSTITUTED PHENYL) BIGUANIDE COMPOUNDS

[75] Inventors: Michael J. Brown, Randolph; Bruce M. Resnick, West Paterson; James H. R. Woodland, Bloomingdale, all of N.J.

[73] Assignee: GAF Corporation, New York, N.Y.

[21] Appl. No.: 945,834

[22] Filed: Sep. 26, 1978

[51] Int. Cl.$^2$ ................. A01N 9/20; C07C 129/12
[52] U.S. Cl. ................. 424/326; 424/303; 424/316; 260/456 A; 260/501.14; 260/565
[58] Field of Search ............. 260/565, 501.14, 456 A; 424/316, 303, 326

[56] References Cited

U.S. PATENT DOCUMENTS

| | | | |
|---|---|---|---|
| 2,508,376 | 5/1950 | Crowther et al. | 260/565 |
| 2,704,710 | 3/1955 | Sprung | 260/565 |
| 3,222,398 | 12/1965 | Brown et al. | 260/565 |
| 3,996,232 | 12/1976 | Diamond et al. | 260/565 |

OTHER PUBLICATIONS

Curd et al., Journal of the Chemical Society (London), pp. 729–737 (1946).

Primary Examiner—Gerald A. Schwartz
Attorney, Agent, or Firm—Walter C. Kehm; Walter Katz

[57] ABSTRACT

The present invention provides novel biguanide compounds for use as agricultural fungicides. The compounds are 1-(alkoxyphenyl)-5-(substituted phenyl) biguanides having the formula:

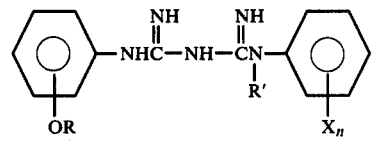

where
R is alkyl $C_4$–$C_{14}$,
R' is hydrogen or alkyl $C_1$–$C_5$,
X is halo, nitro, cyano, trihalomethyl, alkyl $C_1$–$C_8$, alkoxy $C_1$–$C_8$, phenoxy, alkoxycarbonyl $C_2$–$C_4$ or acyl $C_1$–$C_4$, and,
n is 1 or 2, and acid addition salts thereof.

The invention further relates to a composition and method for controlling pathogenic fungi with a fungicidally effective amount of said compound.

12 Claims, No Drawings

FUNGICIDAL 1-(ALKOXYPHENYL)-5-(SUBSTITUTED PHENYL) BIGUANIDE COMPOUNDS

BACKGROUND OF THE INVENTION

1. Field of the Invention

This invention relates to 1-(alkoxyphenyl)-5-(substituted phenyl) biguanide compounds for use as agricultural fungicides.

2. Description of the Prior Art

U.S. Pat. No. 2,704,710 discloses a related biguanide compound which can render azo dyes in color photographic emulsions fast to diffusion. However, this compound is a 5-(unsubstituted phenyl) biguanide and no agricultural fungicidal activity or use is disclosed or suggested for such compound.

U.S. Pat. No. 3,222,398 describes alkoxy substituted monophenylbiguanide compounds only. The compounds are used for their mycobacteriostatic activity, including bacteriostatic and fungistatic activity, against skin and spoilage fungi; however, no use is mentioned for such compounds as agricultural fungicides.

biguanides Chem. Soc. (1946) 729 describes specific related biguanides as antimalarials, and Biochem. Pharmacology 11,995 (1962) discloses such biguanies as useful against skin fungi. These compounds, however, are not active as agricultural fungicides.

SUMMARY OF THE INVENTION

The present invention provides novel biguanide compounds for use as agricultural fungicides. The compounds are 1-(alkoxyphenyl)-5-(substituted phenyl) biguanides having the formula:

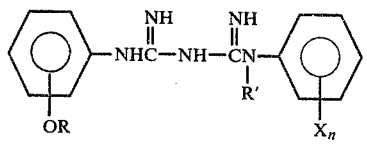

where

R is alkyl $C_4$–$C_{14}$,

R' is hydrogen or alkyl $C_1$–$C_5$,

X is halo, nitro, cyano, trihalomethyl, alkyl $C_1$–$C_8$, alkoxy $C_1$–$C_8$, phenoxy, alkoxycarbonyl $C_2$–$C_4$ or acyl $C_1$–$C_4$, and, n is 1 or 2, and acid addition salts thereof.

The invention further relates to a composition and method for controlling pathogenic fungi with a fungicidally effective amount of said compound.

The term "alkyl", as used herein, includes both linear and branched chain groups, and "halo" is chloro, bromo, iodo or fluoro.

DESCRIPTION OF THE PREFERRED EMBODIMENTS

Two related routes may be used to prepare the compounds of the invention, both of which employ sodium dicyanamide as a starting material. In Method A, which is outlined below, an alkoxy aniline (I) is reacted with sodium dicyanamide (II) to form an alkoxyphenyldicyandiamide intermediate (III). The intermediate (III) then is condensed with a substituted aniline (IV) to form the desired 1-(alkoxyphenyl)-5-(substituted phenyl) biguanide compounds (V) of the invention.

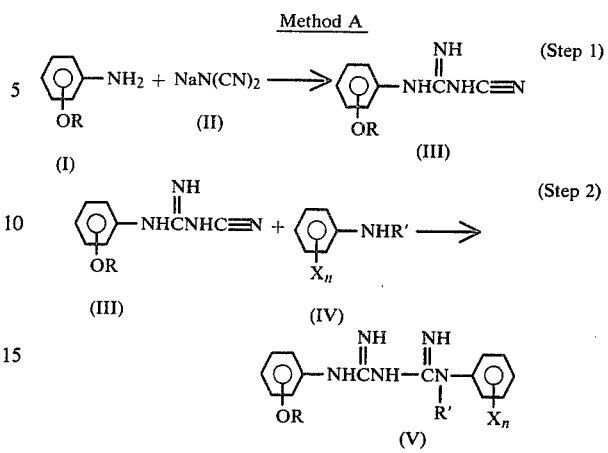

In Method B, the starting material is the substituted aniline (IV), and it is reacted first with sodium dicyanamide to form the intermediate (VI), which is condensed with an alkoxyaniline to form the desired product.

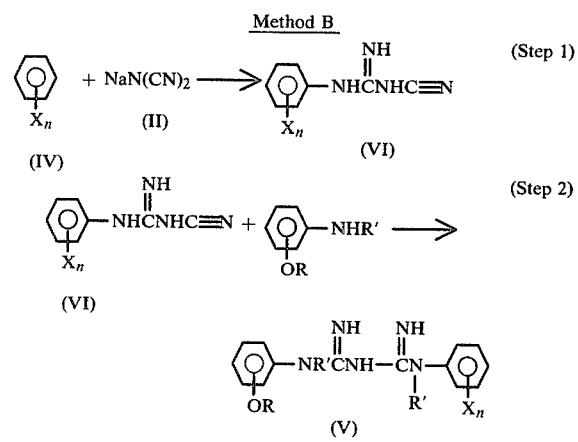

When X is alkoxy, then two moles of the alkoxyaniline may be reacted with sodium dicyanamide to form the biguanide compound directly.

The alkoxyaniline starting materials generally are available commercially; otherwise they may be prepared from the corresponding o-, m-, or p- hydroxyaniline by alkylation with an appropriate alkyl halide in basic solution, as described in Ber. 3, 780(1870). The substituted anilines used as starting materials also are available commercially.

Although the compounds herein may be employed as the free base, the acid addition salt thereof also may be used. For example, such salts as the halides, e.g. chloride, bromide or iodide; acetate, sulfate, hydrogen sulfate, methyl sulfate, benzene sulfonate, p-toluene sulfonate, nitrate and phosphate, are suitable acid addition salts.

The fungicidal compounds of the invention generally are applied as a composition containing a fungicidally effective amount thereof in an inert carrier. The formulation may take the form of a solution, a suspension, emulsion, wettable powder or dust for treating the foilage of the plants, or the fruit itself, or for addition to the soil. Preferably the compositions are applied as a spray of a liquid formulation. The active compound suitably is present in a concentration of about 20 to 5,600 ppm; and about 50 to 500 ppm is a particularly effective amount.

Suitable inert carriers for use in the compositions of the invention include liquid or solid carriers. Suitable liquid carriers include water, acetone, dimethylsulfoxide, alcohols, such as methanol, propylene glycol, and diethylene glycol; N-methylpyrrolidone, isoparaffinic hydrocarbons, such as naphtha or kerosene; ethyl ether, formamide, methylformamide, and mixtures thereof, although many other available solvents may be used as well. Solid carriers or powder diluents may be used when the composition is applied as a dust.

It has been found that the compounds of this invention are useful for the control of fungi which infect many living plants. By way of example only, they are illustrated as effective for controlling such agricultural fungi as bean rust and cucumber anthracnose. However, they may be used also for controlling fungi which affect fruit trees, such as the causative agents for apple scab. They may be utilized in the protective or eradicative modes for various fungi.

To prepare the fungicidal compositions as a liquid formulation suitable for spraying, the active compound first is added to a blend of a dispersant and a surfactant dissolved in a suitable solvent which form a liquid concentrate. Then the concentrate is diluted with water to provide the desired concentration of the active ingredient of the composition for spraying in the field. In a typical preparation of such a spray formulation, a concentrate containing the active ingredient in an amount of about 10%, and the surfactant-dispersant, of about 8%, by weight, in acetone as a solvent, is diluted with water so that the active ingredient is present in the 20–5,600 ppm concentration range.

Alternatively, a wettable powder emulsion may be prepared for spraying directly onto the foliage or to the soil. The wettable powder may be made by admixing the active ingredient, for example, bentonite, chalk, clay, diatomaceous earth, fuller's earth, mica, silica, talc, ground slate, or any of the other usual extenders for agricultural chemicals, and incorporating wetting agents, and/or dispersing agents in such mixtures. The wettable powder then is diluted with water to form a liquid emulsion suitable for spraying.

The surfactants and other wetting agents, and dispersants, which may be included in the spray composition, insure complete contact with the fungus. Conventional nonionic surfactants which provide good wetting of the spray solution on the plant foliage include alkyl polyoxyethylene ethers, polyoxyethylene (20) sorbitan monolaurate, polyoxyethylene (20) sorbitan monoleate, alkylarylpolyglycol ethers, alkyl phenol ethoxylates, trimethyl nonyl polyethylene glycol ethers, alkyl phenol ethylene oxide condensates, octyl phenoxy polyethoxy ethanols, nonylphenyl polyeythylene glycol ethers, condensates of polyoxy ethylenes, polyoxy propylenes, aliphatic polyethers, aliphatic polyesters, alkylaryl polyoxyethylene glycols, and the like.

Suitable dispersing agents include the calcium salt of a polymerized alkyl aryl sulfonic acid, sodium lignosulfonate, or sodium salt of condensed naphthalene sulfonic acid. About 1% to 5%, by weight, of a surfactant, such as polyoxyethylated vegetable oil, alkyl phenoxy polyoxyethylene ethanol, sodium alkyl naphthalene sulfonate often may also be blended with the dispersant formulation.

A typical emulsifier blend of surfactant and dispersing agent is Atlox 3404F, made by ICI America, which is a blend of a calcium sulfonate dispersant and a nonionic surfactant.

Alternatively, the compositions may be applied as a dust of particulate matter comprising the active ingredient in a solid powder, such as one or more of the above-mentioned extender diluents.

The fungicidal compositions generally are applied at a selected rate, preferably until the plants are drenched with the liquid spray, in an amount which will depend upon several prevailing circumstances, such as the susceptibility of the plants to the fungus, the weather, the stage of growth and various other factors.

The present invention herein is further illustrated by the following examples, which are representative but are not to be taken as limiting of the invention.

EXAMPLE 1

1-(o-Octyloxyphenyl)-5-(Iodophenyl) Biguanide

Method A
(Step 1)

A mixture of 12.90 g. of o-Octyloxyaniline hydrochloride and 5.0 g. sodium dicyanamide were dissolved in 150 ml. ethanol and 50 ml water. After refluxing the mixture for three hours the solution was basified with 10% sodium hydroxide to a pH of 9. The solvent then was removed by flash evaporation. The residue was washed with water and extracted with ether. The ether layer was dried over magnesium sulfate, filtered and flash evaporated to yield a tacky substance which solidified upon addition of petroleum ether. After filtering and drying the product weighed 14.0 g. (97% yield).

(Step 2)

A mixture of 2.19 g. of p-iodoanline, 2.88 g. of o-octyloxylphenyldicyandiamide, prepared in Step 1, and 1.0 ml concentrated hydrochloric acid was dissolved into 50 ml. ethanol and refluxed overnight. After neutralization with 10% sodium hydroxide the solvent was removed by flash evaporation. Water was added and the product was extracted with chloroform. This solution was dried over magnesium sulfate, filtered, and flash evaporated to yield a brownish oil (3.10 g., 61% yield).

EXAMPLE 2

1-(p-Octyloxyphenyl)-5-(2-Ethoxycarbonylphenyl) Biguanide

Method B
(Step 1)

Ethyl p-aminobenzoate (8.25 g.) was dissolved in ethanol and 4.0 ml concentrated hydrochloric acid was added. To this suspension was added sodium dicyanamide (4.9 g.) and the reaction mixture was refluxed for 16 hours. Upon cooling the solution solidified, the entire mixture then was placed into 200 ml water and brought to a pH of 10. Filtration yielded a white powder weighing 10.5 g. (81% yield).

(Step-2)

A mixture of 6.1 g. of p-ethoxycarbonylphenyldicyandiamide prepared in Step 1, and 6.8 g. of p-octyloxyaniline hydrochloride were dissolved in 75 ml. ethanol. The solution was refluxed for 16 hours and then the reaction mixture was decanted into 200 ml water. After chilling, the mixture was neutralized and filtered. The yield of product after drying was 4.5 g. (41%) m.p. 234–6° C.

EXAMPLE 3

Following the procedures of Examples 1 and 2 (Methods A or B), using the listed alkoxyanilines and substituted anilines given in Table I below, there is produced the corresponding biguanide products.

TABLE I

| Starting Materials Alkoxyaniline | Substituted Aniline | Product 1-(Alkoxyphenyl)-5-(Substituted phenyl) Biguanide | Prepm. A or B | Compound No. |
|---|---|---|---|---|
| p-n-butyl | p-n-butyloxy | 1,5-bis(p-butyloxy) | A | 1 |
| p-n-pentyl | p-n-pentyloxy | 1,5-bis(p-pentyloxy) | A | 2 |
| p-n-hexyl | p-n-hexyloxy | 1,5-bis(p-hexyloxy) | A | 3 |
| p-n-octyl | p-n-octyloxy | 1,5-bix(p-octyloxy) | A | 4 |
| p-n-octyl | 3,4-dichloro | 1-(p-octyl)-5-(3',4'-dichloro) | A | 5 |
| p-n-octyl | m-trifluoromethyl | 1-(p-octyl)-5-(m-trifluoromethyl) | A | 6 |
| p-n-octyl | m-cyano | 1-(p-octyl)-5-(m-cyano) | B | 7 |
| p-n-octyl | P-butyl | 1-(p-octyl)-5-(p-butyl) | B | 8 |
| p-n-octyl | m-acetyl | 1-(p-octyl)-5-(m-acetyl) | B | 9 |
| p-n-octyl | o-ethoxy | 1-(p-octyl)-5-(o-ethoxy) | A | 10 |
| p-n-octyl | p-fluoro | 1-(p-octyl)-5-(p-fluoro) | A | 11 |
| p-n-octyl | m-nitro | 1-(p-octyl)-5-(m-nitro) | B | 12 |
| p-n-octyl | m-chloro | 1-(p-octyl)-5-(m-chloro) | A | 13 |
| p-n-octyl | p-chloro | 1-(p-octyl)-5-(p-chloro) | A | 14 |
| p-n-octyl | p-carboethoxy | 1-(p-octyl)-5-(p-carboethoxy) | B | 15 |
| p-n-octyl | p-phenoxy | 1-(p-octyl)-5-(p-phenoxy) | A | 16 |
| m-n-octyl | N-methyl-p-methoxy | 1-(m-octyl)-5-(N-methyl-p-methoxy) | A | 17 |
| m-n-octyl | p-methoxy | 1-(m-octyl)-5-(p-methoxy) | A | 18 |
| m-n-octyl | p-nitro | 1-(m-octyl)-5-(p-nitro) | A | 19 |
| o-n-octyl | p-nitro | 1-(o-octyl)-5-(p-nitro) | A | 20 |
| o-n-octyl | p-iodo | 1-(o-octyl)-5-(p-iodo) | A | 21 |
| o-n-octyl | 3,4-dimethyl | 1-(o-octyl)-5-(3',4'-dimethyl) | A | 22 |

EXAMPLE 4

Foliar Fungicidal Tests

For these tests, a suspension of the active ingredient at various concentrations was prepared in a mixture of acetone, water and surfactant. The surfactant was maintained at a constant level at all concentrations. The suspension was made from a standard solution of Triton X-155 surfactant (Rohm and Haas Co.), 1000 ppm in acetone, which was used to dissolve the active compound. The concentrated standard solution then was further diluted with water (1:9) to obtain a diluted stock solution which was a mixture of 10% acetone and 100 ppm of the surfactant in water. This diluted stock solution was used for further dilution of the dissolved compound solution for testing at various concentrations of active material. In this manner, a constant ratio of surfactant was maintained at all compound concentration levels used in the tests.

A. Bean Rust

The compounds were tested on bean rust as follows: Pinto beans grown in 2.5 inch clay pots for 9 to 12 days were sprayed with test liquid suspensions while the plants were rotating on a turntable. About 100 ml. of each suspension was sprayed on the plants. After the spray deposit dried, the plants were atomized with a colloidal suspension of the causative pathogen, and placed in a moist chamber at 70° F. for 24 hours. After 7 to 9 days, the severity of the pustule formation was rated on a scale of 0 (no reduction) to 10 (complete elimination of infection). The results were compared with the commercial fungicide Vitavax, whose active ingredient is carboxin.

The compounds were tested on cucumber plants grown in 2.5 inch pots for 9–12 days by foliage spray. The foliage was sprayed with 100 ml of a 260 ppm formulation while the plants were rotating on a turntable. After the spray deposit dried, the treated plants were inoculated with a colloidal suspension of conidia in water, and placed in a moist chamber at 24° C. for 24 hours. Four days after inoculation, the number of lesions was counted, and a rating was calculated on a scale of 0 (no control) to 10 (100% control). Daconil was used as a foliar standard. The foliar treatments were applied also at 130 and 65 and 33 ppm.

TABLE II
Bean Rust Fungitoxicity Ratings

| Compound No. Conc. ppm | 1 | 4 | 5 | 6 | 8 | 9 | 10 | 11 | 13 | 14 | 15 | 16 | 19 | 20 | 22 | Standards Vitavax | Arasan |
|---|---|---|---|---|---|---|---|---|---|---|---|---|---|---|---|---|---|
| 260 | 10 | 10 | 10 | 10 | 9 | 10 | 9 | 10 | 10 | 10 | 10 | 9 | 10 | 10 | 10 | 9 | |
| 130 | 9.5 | | 10 | 10 | 9 | 9 | 9 | | 9 | 9 | 9 | | | 8 | 9 | 9 | |
| 65 | 9.5 | | 10 | 10 | 9 | 8 | 9 | | 8 | 9 | 9 | | | 8 | 8 | 9 | |
| 33 | 10 | | 9 | 10 | 8 | 6 | 9 | | 9 | 9 | 9 | | | 8 | 8 | 9 | 9 |
| 16 | 10 | | 8 | 8 | | | | | 9 | 8 | | | | | | | 9 |
| 8 | 8.5 | | 8 | 8 | | | | | 9 | 6 | | | | | | | 9 |

III
Cucumber Anthracnose Fungitoxicity Ratings

| Conc. ppm | Compound No. | | | | | | | | | | |
|---|---|---|---|---|---|---|---|---|---|---|---|
| | 1 | 5 | 6 | 8 | 10 | 13 | 14 | 15 | 20 | 22 | Daconil |
| 260 | 9 | 9 | 8 | 9 | 8 | | 9 | 8 | 9 | 8 | 9 |

-continued

| 130 | 8 | 9 | 7 | 7 | 4 | 9 | 9 | 8 | 5 | 2 | 9 |
| 65 | 7 | 0 | 4 | 9 | 3 | 9 | 8 | 1 | 5 | 3 | 8 |

What we claimed is:

1. A method of protecting living plants, comprising contacting said plant with a fungicidally acceptable amount of 1-(alkoxyphenyl)-5-(substituted phenyl) biguanides having the formula:

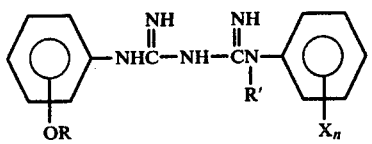

wherein
R is alkyl $C_4$–$C_{14}$,
R' is hydrogen or alkyl $C_1$–$C_5$,
X is halo, nitro, cyano, trihalomethyl, alkyl $C_1$–$C_8$, alkoxy $C_1$–$C_8$, phenoxy, alkoxycarbonyl $C_2$–$C_4$ or acetyl,
n is 1 or 2, and, fungicidally acceptable acid addition salts thereof.

2. An agricultural fungicidal composition of matter comprising a fungicidally effective amount of a compound of the formula of claim 1 and an inert carrier.

3. Composition according to claim 2 wherein R is alkyl $C_4$–$C_{14}$.

4. Composition according to claim 2 wherein R' is hydrogen.

5. Composition according to claim 2 wherein R' is alkyl $C_1$–$C_5$.

6. Composition according to claim 2 wherein X is halo.

7. Compositions according to claim 2 wherein X is alkoxy $C_1$–$C_8$.

8. Composition according to claim 2 wherein n is 1.

9. Composition according to claim 2 wherein n is 2.

10. A composition according to claim 2 which is 1,5-bis (p-butoxyphenyl) biguanide.

11. A composition according to claim 2 which is 1-(p-octyloxyphenyl)-5-(m-chlorophenyl) biguanide.

12. A composition according to claim 2 which is 1-(p-octyloxyphenyl)-5-(p-chlorophenyl) biguanide.

* * * * *